United States Patent
Wang et al.

(10) Patent No.: US 11,332,471 B2
(45) Date of Patent: May 17, 2022

(54) LEVELING AGENT, METAL PLATING COMPOSITION CONTAINING SAME, PREPARATION METHOD THEREFOR AND USE THEREOF

(71) Applicant: SHANGHAI SINYANG SEMICONDUCTOR MATERIALS CO., LTD., Shanghai (CN)

(72) Inventors: Su Wang, Shanghai (CN); Liqi Shi, Shanghai (CN); Xuepeng Gao, Shanghai (CN)

(73) Assignee: SHANGHAI SINYANG SEMICONDUCTOR MATERIALS CO., LTD., Shanghai (CN)

( * ) Notice: Subject to any disclaimer, the term of this patent is extended or adjusted under 35 U.S.C. 154(b) by 289 days.

(21) Appl. No.: 16/462,333

(22) PCT Filed: Dec. 15, 2017

(86) PCT No.: PCT/CN2017/116441
§ 371 (c)(1),
(2) Date: May 20, 2019

(87) PCT Pub. No.: WO2019/019532
PCT Pub. Date: Jan. 31, 2019

(65) Prior Publication Data
US 2019/0367522 A1    Dec. 5, 2019

(30) Foreign Application Priority Data
Jul. 25, 2017 (CN) .......................... 201710613256.3

(51) Int. Cl.
*C25D 3/38* (2006.01)
*C07D 487/04* (2006.01)

(52) U.S. Cl.
CPC ............ *C07D 487/04* (2013.01); *C25D 3/38* (2013.01)

(58) Field of Classification Search
None
See application file for complete search history.

(56) References Cited

FOREIGN PATENT DOCUMENTS

| | | |
|---|---|---|
| CN | 100529194 C | 8/2009 |
| CN | 102276796 A | 12/2011 |
| CN | 105683250 A | 6/2016 |
| CN | 105705491 A | 6/2016 |
| CN | 106432247 A | 2/2017 |
| CN | 107217283 A | 9/2017 |
| CN | 107313082 A | 11/2017 |
| EP | 2366686 A2 | 9/2011 |
| WO | 2007135380 A2 | 11/2007 |
| WO | 2009034386 A1 | 3/2009 |
| WO | 2015066848 A1 | 5/2015 |

OTHER PUBLICATIONS

International Search Report and Written Opinion of PCT/CN2017/116441 dated Apr. 19, 2018.

*Primary Examiner* — Stefanie S Wittenberg

(57) ABSTRACT

Disclosed are a leveling agent, a metal plating composition containing same, and a preparation method therefor and the use thereof. The raw materials of the metal electroplating composition comprise a metal plating solution and a leveling agent; the metal plating solution comprises a copper salt, an acidic electrolyte, a source of halide ions and water; and the leveling agent is a compound of formula I. The metal plating composition can be used in the processes of printed circuit board electroplating and integrated circuit copper interconnection electroplating, can achieve the effects of no voids or defects, low purity in the plating layer, good plating homogeneity, a dense structure and small surface roughness, and has better industrial application value.

14 Claims, No Drawings

LEVELING AGENT, METAL PLATING COMPOSITION CONTAINING SAME, PREPARATION METHOD THEREFOR AND USE THEREOF

CROSS-REFERENCE TO RELATED APPLICATIONS

This application is a 371 National Phase of PCT/CN2017/116441 filed Dec. 15, 2017, which claims the benefit of Chinese Patent Application No. 201710613256.3, filed on Jul. 25, 2017. The entire disclosures of the above applications are incorporated herein by reference.

FIELD OF INVENTION

The present invention relates to the field of semiconductor materials, specifically relates to a leveling agent, metal electroplating composition containing the same, preparation method and uses thereof.

PRIOR ARTS

With the development of Very Large Scale Integration (VLSI) and Ultra Large Scale Integration (ULSI), the integration is increasing and the circuit components are getting denser and denser, chip interconnection becomes a key factor affecting the chip performance. The reliability of the interconnect structures is crucial to the success of VLSI and ULSI and the increase in circuit density. However, due to size limitations of the circuitry, the size reduction of interconnects in VLSI and ULSI technologies has raised additional demands on the processing capacity, which comprise the precise processing of multilayer, high aspect ratio structural features.

The width, aperture size, and other feature size of the interconnect decrease with the increase of circuit density. However, the thickness of the dielectric layer will not decrease proportionally. As a result, the aspect ratio feature increases. Secondly, in the back end of line process of integrated circuits, copper has gradually replaced aluminum as the predominant material used in interconnect technology of VLSI interconnection. In current chip manufacturing, the wiring and interconnection of the chip are almost entirely copper plated.

Copper has a lower resistivity (about 35% lower) and a higher resistance to electromigration (about twice as aluminum) than aluminum. Moreover, copper has good thermal conductivity, which is advantageous to the devices of multilayer integration with higher circuit density and current density. Copper can be coated on the substrate by electroplating, sputtering, physical vapor deposition, and chemical vapor deposition. The damascene process (Damascus process) in the form of electroplating is generally considered to be the best method for preparing copper interconnects. The copper damascene process can be filled with micronanoscale pores by electroplating, which has the characteristics of high deposition speed and low cost.

However, with the continuous development of the integrated circuit technology, the requirements for filling the pores of nanoscale are becoming more stringent. Researchers from all over the world are eager to study electroplating methods, electroplating solutions and additives for printed circuit board plating and integrated circuit copper interconnect plating processes to achieve the effects that no hole or defect exists between the metal plating layers, low plating layer impurity, good uniform-plating property, compact structure, and small surface roughness.

Generally, the leveling agents for copper plating can better level the sediment across the surface of the substrate, but tend to impair the uniform-plating capacity of the plating bath. The uniform-plating capacity is defined as the ratio of the thickness of the copper sediment in the center of the pore to the thickness at its surface.

Patent Application No. CN105683250A has disclosed a polymer leveling agent comprising an imidazole structure, which can be used to solve the problem of uniform-plating on PCB plating. However, it is not effective in the application of nano scale Damascus copper interconnect plating.

Therefore, there is an urgent need in the art to develop electroplating methods, electroplating solutions and additives used for printed circuit board electroplating and integrated circuit copper interconnection electroplating processes, which achieve the effects that no hole or defect between the metal plating layers, low plating layer impurity, good uniform-plating property, compact structure, and small surface roughness.

CONTENT OF THE PRESENT INVENTION

An object of the present invention is to provide a leveling agent, metal electroplating composition containing the same, preparation method and uses thereof, in order to solve the problem that the metal plating layers made by the prior electroplating method, electroplating solution and additives have holes and defects, high plating layer impurity, poor uniform-plating property, poor structure density, and rough surface. The leveling agent and the metal electroplating composition containing the leveling agent can be used for printed circuit board electroplating and integrated circuit copper interconnection electroplating processes, which can achieve the effects of no hole or defect in the metal plating layers, low plating layer impurity, good uniform-plating property, compact structure and small surface roughness, and has better industrial application value.

The present invention solves the above technical problems by the following technical solutions.

The first aspect of the present invention provides a use of the compound of formula I as a leveling agent in metal electroplating composition

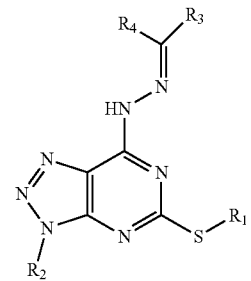

wherein,
$R_1$ is $C_1$-$C_5$ alkyl, propargyl, allyl or benzyl;
$R_2$ is H, $C_1$-$C_5$ alkyl, hydroxy-substituted $C_1$-$C_5$ alkyl, unsaturated five-membered heterocyclic substituted $C_1$-$C_3$ alkyl, phenyl, halogenated phenyl, benzyl, halogenated benzyl or a hydroxyl-substituted benzyl;

$R_3$ is substituted or unsubstituted phenyl, pyridyl, naphthyl, hydroxy-substituted naphthyl, thienyl, furyl or indolyl;

$R_4$ is H or $C_1$-$C_5$ alkyl;

The substituent of the substituted phenyl is selected from the group consisting of halogen, $C_1$-$C_5$ alkyl, nitro, methoxy, hydroxy and $C_1$-$C_3$ alkylamino; the substituents are the same or different when there are more than one substituents attached;

the heteroatom in the unsaturated five-membered heterocyclic ring is selected from the group consisting of O, N and S, and the number of heteroatoms is 1 to 3, the heteroatoms are the same or different when there are more than one heteroatoms.

In the use, preferably, $R_1$ is methyl, propyl, benzyl, propargyl or allyl;

preferably, $R_2$ is benzyl, methyl, hydroxyethyl, thiophene-substituted methyl, furan-substituted ethyl, monohalogenated benzyl (such as (such as [structures of chlorobenzyl, bromobenzyl, fluorobenzyl groups]), or hydroxy-substituted benzyl (such as (such as [4-hydroxybenzyl structure] OH);

preferably, $R_3$ is pyridyl (such as (such as [pyridyl structure]), thienyl (such as (such as [thienyl structure]), indolyl (such as (such as [indolyl structure]), naphthyl (such as (such as [naphthyl structure]), hydroxy-substituted naphthyl (such as (such as [hydroxynaphthyl structure]), phenyl, hydroxy-substituted phenyl (such as (such as [2-hydroxyphenyl structure] or [4-hydroxyphenyl structure]), monohalogenated phenyl (such as (such as [structures of chlorophenyl and bromophenyl groups]) or methylphenyl (such as (such as ![p-tolyl]), nitrophenyl (such as (such as 4-NO₂-phenyl), methoxyphenyl (such as (such as 3,4,5-trimethoxyphenyl or 4-methoxyphenyl), or dimethylamino-substituted phenyl (such as (such as 4-N(CH₃)₂-phenyl);

preferably, $R_4$ is H or methyl;
the use, wherein,
the leveling agent is preferably selected from the group consisting of:
Compound 1: $R_1$=Propyl-; $R_2$=Bn-; $R_3$=Ph-; $R_4$=H—;
Compound 2: $R_1$=Propyl-; $R_2$=Bn-; $R_3$=2-Cl-Ph-; $R_4$=H—;
Compound 3: $R_1$=Propyl-; $R_2$=Bn-; $R_3$=3-Cl-Ph-; $R_4$=H—;
Compound 4: $R_1$=Propyl-; $R_2$=Bn-; $R_3$=4-Cl-Ph-; $R_4$=H—;
Compound 5: $R_1$=Propyl-; $R_2$=Bn-; $R_3$=4-Br-Ph-; $R_4$=H—;
Compound 6: $R_1$=Propyl-; $R_2$=Bn-; $R_3$=2-F-Ph-; $R_4$=H—;
Compound 7: $R_1$=Propyl-; $R_2$=Bn-; $R_3$=4-Me-Ph-; $R_4$=H—;
Compound 8: $R_1$=Propyl-; $R_2$=Bn-; $R_3$=3,4,5-(MeO)₃-Ph-; $R_4$=H—;
Compound 9: $R_1$=Propyl-; $R_2$=Bn-; $R_3$=4-NO₂-Ph-; $R_4$=H—;
Compound 10: $R_1$=Propyl-; $R_2$=Bn-; $R_3$=4-(N,N—(CH₃)₂)-Ph-; $R_4$=H—;
Compound 11: $R_1$=Propyl-; $R_2$=Bn-;

$R_3$ = (2-thienyl);

$R_4$=H—;
Compound 12: $R_1$=Propyl-; $R_2$=Bn-;

$R_3$ = (3-indolyl);

$R_4$=H—;
Compound 13: $R_1$=Propyl-; $R_2$=Bn-;

$R_3$ = (1-(2-hydroxynaphthyl));

$R_4$=H—;
Compound 14: $R_1$=Propyl-; $R_2$=Bn-;

$R_3$ = (2-naphthyl);

$R_4$=H—;
Compound 15: $R_1$=Propyl-; $R_2$=Bn-;

$R_3$ = (3-pyridyl);

$R_4$=H—;

Compound 16: $R_1$=Propyl-; $R_2$=Bn-; $R_3$=Ph-; $R_4$=CH$_3$—;

Compound 17: $R_1$=Propyl-; $R_2$=Bn-; $R_3$=4-MeO-Ph-; $R_4$=CH$_3$—;

Compound 18: $R_1$=Propyl-; $R_2$=Bn-; $R_3$=2-OH-Ph-; $R_4$=CH$_3$—;

Compound 19: $R_1$=Propyl-; $R_2$=Bn-; $R_3$=4-OH-Ph-; $R_4$=CH$_3$—;

Compound 20: $R_1$=Propyl-; $R_2$=Bn-; $R_3$=4-Br-Ph-; $R_4$=CH$_3$—;

Compound 21: $R_1$=Propyl-;

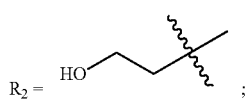

$R_3$=2-OH-Ph-; $R_4$=CH$_3$—;

Compound 22: $R_1$=Propyl-; $R_2$=2-Cl-Bn-; $R_3$=2-OH-Ph-; $R_4$=CH$_3$—;

Compound 23: $R_1$=Propyl-; $R_2$=3-Cl-Bn-; $R_3$=2-OH-Ph-; $R_4$=CH$_3$—;

Compound 24: $R_1$=Propyl-; $R_2$=4-Cl-Bn-; $R_3$=2-OH-Ph-; $R_4$=CH$_3$—;

Compound 25: $R_1$=Propyl-; $R_2$=4-Br-Bn-; $R_3$=2-OH-Ph-; $R_4$=CH$_3$—;

Compound 26: $R_1$=Propyl-; $R_2$=4-F-Bn-; $R_3$=2-OH-Ph-; $R_4$=CH$_3$—;

Compound 27: $R_1$=Propyl-;

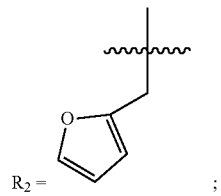

$R_3$=2-OH-Ph-; $R_4$=CH$_3$—;

Compound 28: $R_1$=Propyl-;

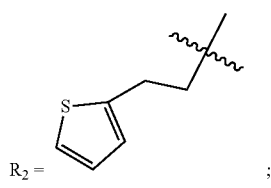 [SMILES: *CCc1cccs1]

$R_3$=2-OH-Ph-; $R_4$=CH$_3$—;

Compound 29: $R_1$=Propyl-; $R_2$=4-OH-Bn-; $R_3$=2-OH-Ph-; $R_4$=CH$_3$—;

Compound 30: $R_1$=Propargyl-; $R_2$=Bn-; $R_3$=3,4,5-(MeO)$_3$-Ph-; $R_4$=H—;

Compound 31: $R_1$=Propargyl-; $R_2$=Bn-;

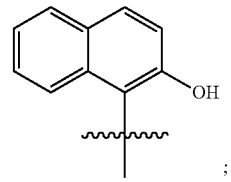

$R_4$=H—;

Compound 32: $R_1$=Propargyl-; $R_2$=Bn-; $R_3$=4-(N,N—(CH$_3$)$_2$)-Ph-; $R_4$=H—;

Compound 33: $R_1$=Propargyl-; $R_2$=Bn-; $R_3$=2-OH-Ph-; $R_4$=CH$_3$—;

Compound 34: $R_1$=Bn-; $R_2$=Bn-; $R_3$=3,4,5-(MeO)$_3$-Ph-; $R_4$=H—; and

Compound 35: $R_1$=Bn-; $R_2$=Bn-; $R_3$=2-OH-Ph-; $R_4$=CH$_3$—.

In the present invention, the compound represented by formula I is prepared in accordance with the method disclosed in Chinese Patent Application CN201610853873.6.

The second aspect of the present invention provides a metal electroplating composition, wherein the raw material of the metal electroplating composition comprises a metal electroplating liquid and the leveling agent as defined in the first aspect of the present invention; the metal electroplating liquid comprises a copper salt, acidic electrolyte, halide ions source and water.

The metal electroplating composition, wherein,

The copper salt is preferably selected from the group consisting of copper sulfate, copper halide, copper acetate, copper nitrate, copper fluoroborate, copper alkylsulfonate, copper aryl sulfonate, copper sulfamate and copper gluconate; the copper alkylsulfonate is preferably selected from the group consisting of copper methanesulfonate, copper ethanesulfonate and copper propanesulfonate; the copper aryl sulfonate is preferably selected from the group consisting of copper phenyl sulfonate, copper phenolsulfonate and copper p-toluenesulfonate. The molar concentration of the copper ions in the metal electroplating liquid is 0.15-2.85 mol/L.

The acidic electrolyte is preferably selected from the group consisting of sulfuric acid, phosphoric acid, acetic acid, fluoroboric acid, sulfamic acid, alkyl sulfonic acid, aryl sulfonic acid and hydrochloric acid. The alkyl sulfonic acid is preferably selected from the group consisting of methanesulfonic acid, ethanesulfonic acid, propanesulfonic acid and trifluoromethanesulfonic acid; the aryl sulfonic acid is preferably selected from the group consisting of phenylsulfonic acid, phenolsulfonic acid and toluenesulfonic acid. In each liter of the metal electroplating composition, the mass of the acidic electrolyte is preferably 1-300 g.

The halide ions source is preferably a chloride ions source. The chloride ions source is preferably selected from the group consisting of copper chloride, tin chloride and hydrochloric acid. The concentration of the halide ions of the halide ions source is preferably 0-100 ppm but not 0, more preferably 50-100 ppm.

In the present invention, the metal electroplating liquid is preferably an electroplating copper solution SYS$^D$2110, and the manufacturer thereof is Shanghai Xinyang Semiconductor Material Co., Ltd. The preparation of SYS$^D$2110 can refer to the method disclosed in Chinese Patent No. CN100529194C.

In the present invention, the raw material of the metal electroplating composition further comprises an accelerator, wherein the accelerator (also referred to as a brightener)

refers to an organic additive capable of increasing the plating rate of the plating bath, and the accelerator is the accelerator acceptable in the art. The accelerator is preferably selected from the group consisting of N,N-dimethyl-disulfenyl carbamic acid-(3-sulfopropyl) ester, 3-mercapto-propylsulfonic acid-(3-sulfopropyl) ester, 3-mercapto-propyl sulfonate sodium salt; disulfenyl carbonate-o-ethyl ester-s-ester and 3-mercapto-1-propane sulfonate potassium salt, disulfopropyl disulfide, 3-(benzothiazolyl-s-sulfenyl)propyl sulfonate sodium salt, pyridinium propyl sulfonyl betaine, 1-sodium-3-mercapto propane-1-sulfonate, N,N-dimethyl-disulfenyl carbamic acid-(3-sulfoethyl) ester, 3-mercapto-ethyl propyl sulfonic acid-(3-sulfoethyl) ester, 3-mercapto-ethyl sulfonate sodium salt, carbonic acid-disulfenyl-o-ethyl ester-s-ester and 3-mercapto-1-ethanesulfonate potassium salt, disulfoethyl disulfide, 3-(benzothiazolyl-s-sulfenyl) ethyl sulfonate sodium salt, pyridinium ethyl sulfonyl betaine and 1-sodium-3-mercaptoethane-1-sulfonate; the concentration of the accelerator is preferably 0.1 ppm-1000 ppm.

In a preferred embodiment of the present invention, the accelerator is UPD3115A, which is applied by Shanghai Xinyang Semiconductor Materials Co., Ltd.

In the present invention, the raw material of the metal electroplating composition further comprises an inhibitor, and the inhibitor refers to an organic additive capable of suppressing the rate of metal electroplating. The inhibitor is preferably selected from the group consisting of polypropylene glycol copolymer, polyethylene glycol copolymer, ethylene oxide-propylene oxide (EO/PO) copolymer and butanol-ethylene oxide-propylene oxide copolymer; the butanol-ethylene oxide-propylene oxide copolymer preferably has a weight-average molecular weight of 100-100,000, more preferably 500-10,000; the concentration of the inhibitor is preferably 1-10000 ppm, more preferably 5-10000 ppm.

In a preferred embodiment of the invention, the inhibitor is UPD3115S, which is applied by Shanghai Xinyang Semiconductor Materials Co., Ltd.

In the present invention, the concentration of the leveling agent is the concentration acceptable in the art, preferably 1-10 ppm, more preferably 5-10 ppm.

In a preferred embodiment of the invention, the raw material of the metal electroplating composition consists of the metal electroplating liquid, the leveling agent, the accelerator and the inhibitor.

The third aspect of the present invention provides a method for preparing the metal electroplating composition as defined in the second aspect of the present invention, which preferably comprises mixing the raw material components uniformly.

The fourth aspect of the present invention provides the use of the metal electroplating composition as defined in the second aspect of the present invention in printed circuit board electroplating and integrated circuit copper interconnection electroplating processes, the use preferably comprises:

(1) contacting the substrate to be electroplated with the metal electroplating composition;

(2) applying an electric current for electroplating.

In step (1), the substrate is any substrate acceptable in the art, preferably a wafer or chip of a printed circuit board or an integrated circuit.

In step (2), the current density of the electroplating is acceptable in the art, preferably 0.1-10 ASD, more preferably 0.3-5 ASD, the most preferably 0.5-1.5 ASD;

in step (2), the electroplating time is acceptable in the art, preferably 53-110 s, preferably 80-110 s.

in step (2), the electroplating temperature is acceptable in the art, preferably 10-65° C., more preferably 10-35° C., the most preferably 20-30° C.

In a preferred embodiment of the invention, step (2) is preferably carried out in three steps:

in the first step, the current density is 0.1-0.5 ASD, more preferably 0.3 ASD; the electroplating time is 3-20 s, more preferably 10 s; the electroplating temperature is 10-65° C., more preferably 10-35° C., the most preferably 20-30° C., for example 25° C.;

in the second step, the current density is 0.5-1.5 ASD, more preferably 1.0 ASD; the electroplating time is 20-30s, more preferably 25s; the electroplating temperature is 10-65° C., more preferably 10-35° C., the most preferably 20-30° C., for example 25° C.;

in the third step, the current density is 1-10 ASD, more preferably 5 ASD; the electroplating time is 30-60s, more preferably 45s; the electroplating temperature is 10-65° C., more preferably 10-35° C., the most preferably 20-30° C., for example 25° C.

In the present invention, the term "Propyl-" refers to propyl, of which structure is

In the present invention, the term "Propargyl-" refers to propargyl, of which structure is

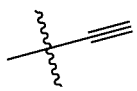

In the present invention, the term "Bn-" refers to benzyl, of which structure is

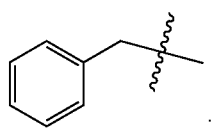 [SMILES: *Cc1ccccc1]

In the present invention, the term "Ph-" refers to phenyl, of which structure is

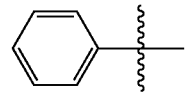

In the present invention, the term "$C_1$-$C_5$ alkyl" is preferably methyl, ethyl, n-propyl, isopropyl, n-butyl, isobutyl, tert-butyl, n-pentyl, isopentyl or neopentyl. Unless otherwise specified, propyl, butyl or pentyl refers to n-propyl, n-butyl or n-pentyl, respectively.

In the present invention, the term "unsaturated five-membered heterocyclic ring" preferably has aromaticity.

The unsaturated five-membered heterocyclic ring is preferably furan, thiophene, pyrazole, imidazole, thiazole, triazole or tetrazolium and the like.

In the present invention, the term "hydroxy-substituted X group" refers to an X group substituted by one or more than one hydroxy (the number of hydroxy depends on the number of H atoms, for example 1-6, preferably 1-3), wherein the position of the hydroxy is optional. For example, "hydroxy substituted benzyl" refers to a benzyl group substituted with one or more hydroxy, including but not limited to

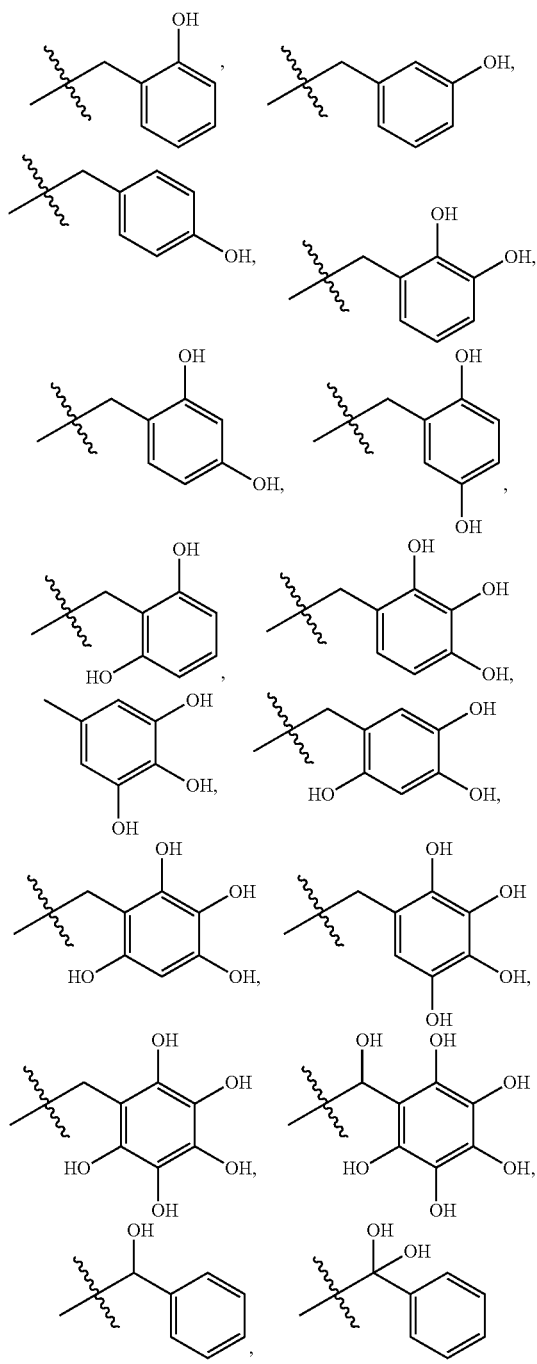

and the like.

In the present invention, the term "halogenated Y group" refers to a Y group substituted by one or more than one halogens (the number of halogens may be determined according to the number of H, for example 1 to 6, preferably 1 to 3). For example, halogenated phenyl refers to a phenyl substituted with one or more than one halogens, wherein the halogens may be the same or different, including but not limited to

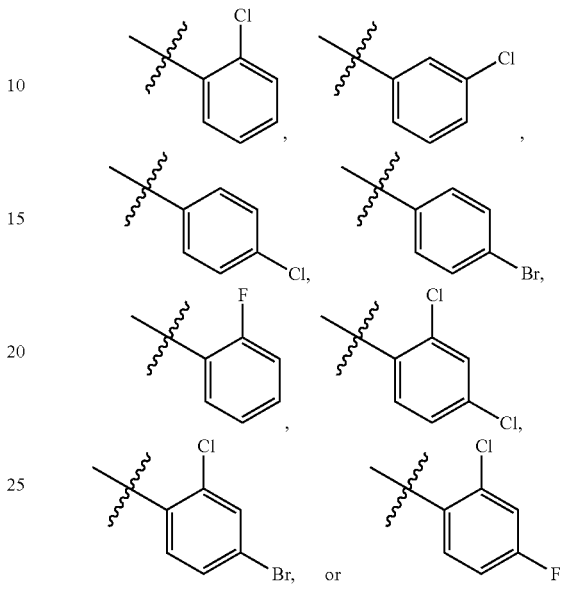

and the like.

In the present invention, the term "halogen" refers to F, Cl, Br or I.

In the present invention, the term "concentration" refers to the concentration of each substance in 1 L metal electroplating liquid.

In the present invention, unless otherwise specified in the context, the following abbreviations should have the following meanings: A=amperes; A/dm2=amps per square decimeter=ASD; ° C.=degrees Celsius; ppm=parts per million. Unless otherwise indicated, all % refer to mass percentage. All numerical ranges are inclusive and can be combined in any order, but it is obvious that the sum of such numerical ranges are limited to 100%.

In the present invention, "feature" refers to the geometry on the substrate. "Aperture" refers to a sunken feature that comprises a through hole and a blind channel. "Halide" refers to fluoride, chloride, bromide and iodide.

In the present invention, the temperature of "ice bath" refers to −5° C.–5° C., preferably −5° C.–0° C.

Based on the common knowledge in the art, the above various preferred conditions can be optionally combined to obtain preferred embodiments of the present invention.

The reagents and raw materials used in the present invention are commercially available.

The positive effects of the present invention are as follows:

the metal electroplating composition of the present invention comprises a leveling agent represented by the formula I. The metal electroplating composition can be used for printed circuit board electroplating and integrated circuit copper interconnection electroplating processes, which achieves the effects of free of holes and defects, low plated layer impurity, good uniform-plating property, compact structure, and small surface roughness. Furthermore, the metal electroplating composition has good thermal reliability and uniform-plating property, and can solve the problem of orifice sealing, and has good industrial application value.

EMBODIMENT

Preparation Embodiments: Preparation of Metal Electroplating Compositions 1-35 and Comparative Metal Electroplating Compositions 1-6

The components of the metal electroplating compositions 1-35 and the comparative metal electroplating compositions 1-6 are shown in Table 1, wherein, the metal ions source and the electrolyte is provided by electroplating copper solution of the trademark SYS$^D$2110, which is purchased from Shanghai Xinyang Semiconductor Materials Co., Ltd. The accelerator of the trademark UPD3115 A is purchased from Shanghai Xinyang Semiconductor Materials Co., Ltd. The inhibitor of the trademark UPD3115S is purchased from Shanghai Xinyang Semiconductor Materials Co., Ltd.

TABLE 1

| Formula No. | Electroplating copper solution | Accelerator | Inhibitor | Leveling agent | Amount of electroplating copper solution | Amount of accelerator | Amount of inhibitor | Amount of leveling agent |
|---|---|---|---|---|---|---|---|---|
| Metal electroplating composition 1 | SYS$^D$2110 | UPD3115 A | UPD3115S | Compound 1 | 1 L | 10 ppm | 100 ppm | 1 ppm |
| Metal electroplaing composition 2 | SYS$^D$2110 | UPD3115 A | UPD3115S | Compound 2 | 1 L | 50 ppm | 500 ppm | 5 ppm |
| Metal electroplating composition 3 | SYS$^D$2110 | UPD3115 A | UPD3115S | Compound 3 | 1 L | 100 ppm | 1000 ppm | 10 ppm |
| Metal electroplating composition 4 | SYS$^D$2110 | N,N-dimethyl-disulfenyl carbamic acid-(3-sulfopropyl)ester | Butanol-ethylene oxide-alkylene oxide, Mw = 1000 | Compound 4 | 1 L | 10 ppm | 100 ppm | 1 ppm |
| Metal electroplating composition 5 | SYS$^D$2110 | 1-sodium-3-mercapto propane-1-sulfonate | Butanol-ethylene oxide-alkylene oxide, Mw = 3000 | Compound 5 | 1 L | 50 ppm | 500 ppm | 5 ppm |
| Metal electroplating composition 6 | SYS$^D$2110 | 3-(benzothiazolyl-s-sulfenyl)propyl sulfonate sodium salt | Butanol-ethylene oxide-alkylene oxide, Mw = 10000 | Compound 6 | 1 L | 100 ppm | 1000 ppm | 10 ppm |
| Metal electroplating composition 7 | SYS$^D$2110 | UPD3115 A | UPD3115S | Compound 7 | 1 L | 10 ppm | 100 ppm | 1 ppm |
| Metal electroplating composition 8 | SYS$^D$2110 | UPD3115 A | UPD3115S | Compound 8 | 1 L | 50 ppm | 500 ppm | 5 ppm |
| Metal electroplating composition 9 | SYS$^D$2110 | UPD3115 A | UPD3115S | Compound 9 | 1 L | 100 ppm | 1000 ppm | 10 ppm |
| Metal electroplating composition 10 | SYS$^D$2110 | N,N-dimethyl-disulfenyl carbamic acid-(3-sulfopropyl)ester | Butanol-ethylene oxide-alkylene oxide, Mw = 1000 | Compound 10 | 1 L | 10 ppm | 100 ppm | 1 ppm |
| Metal electroplating composition 11 | SYS$^D$2110 | 1-sodium-3-mercapto propane-1-sulfonate | Butanol-ethylene oxide-alkylene oxide, Mw = 3000 | Compound 11 | 1 L | 50 ppm | 500 ppm | 5 ppm |
| Metal electroplating composition 12 | SYS$^D$2110 | 3-(benzothiazolyl-s-sulfenyl)propyl sulfonate sodium salt | Butanol-ethylene oxide-alkylene oxide, Mw = 10000 | Compound 12 | 1 L | 100 ppm | 1000 ppm | 10 ppm |
| Metal electroplating composition 13 | SYS$^D$2110 | UPD3115 A | UPD3115S | Compound 13 | 1 L | 10 ppm | 100 ppm | 1 ppm |

TABLE 1-continued

| Formula No. | Electroplating copper solution | Accelerator | Inhibitor | Leveling agent | Amount of electroplating copper solution | Amount of accelerator | Amount of inhibitor | Amount of leveling agent |
|---|---|---|---|---|---|---|---|---|
| Metal electroplating composition 14 | SYS$^D$2110 | UPD3115 A | UPD3115S | Compound 14 | 1 L | 50 ppm | 500 ppm | 5 ppm |
| Metal electroplating composition 15 | SYS$^D$2110 | UPD3115 A | UPD3115S | Compound 15 | 1 L | 100 ppm | 1000 ppm | 10 ppm |
| Metal electroplating composition 16 | SYS$^D$2110 | N,N-dimethyl-disulfenyl carbamic acid-(3-sulfopropyl)ester | Butanol-ethylene oxide-alkylene oxide, Mw = 1000 | Compound 16 | 1 L | 10 ppm | 100 ppm | 1 ppm |
| Metal electroplating composition 17 | SYS$^D$2110 | 1-sodium-3-mercapto propane-1-sulfonate | Butanol-ethylene oxide-alkylene oxide, Mw = 3000 | Compound 17 | 1 L | 50 ppm | 500 ppm | 5 ppm |
| Metal electroplating composition 18 | SYS$^D$2110 | 3-(benzothiazolyl-s-sulfenyl)propyl sulfonate sodium salt | Butanol-ethylene oxide-alkylene oxide, Mw = 10000 | Compound 18 | 1 L | 100 ppm | 1000 ppm | 10 ppm |
| Metal electroplating composition 19 | SYS$^D$2110 | UPD3115 A | UPD3115S | Compound 19 | 1 L | 10 ppm | 100 ppm | 1 ppm |
| Metal electroplating composition 20 | SYS$^D$2110 | UPD3115 A | UPD3115S | Compound 20 | 1 L | 50 ppm | 500 ppm | 5 ppm |
| Metal electroplating composition 21 | SYS$^D$2110 | UPD3115 A | UPD3115S | Compound 21 | 1 L | 100 ppm | 1000 ppm | 10 ppm |
| Metal electroplating composition 22 | SYS$^D$2110 | N,N-dimethyl-disulfenyl carbamic acid-(3-sulfopropyl)ester | Butanol-ethylene oxide-alkylene oxide, Mw = 1000 | Compound 22 | 1 L | 10 ppm | 100 ppm | 1 ppm |
| Metal electroplating composition 23 | SYS$^D$2110 | 1-sodium-3-mercapto propane-1-sulfonate | Butanol-ethylene oxide-alkylene oxide, Mw = 3000 | Compound 23 | 1 L | 50 ppm | 500 ppm | 5 ppm |
| Metal electroplating composition 24 | SYS$^D$2110 | 3-(benzothiazolyl-s-sulfenyl)propyl sulfonate sodium salt | Butanol-ethylene oxide-alkylene oxide, Mw = 10000 | Compound 24 | 1 L | 100 ppm | 1000 ppm | 10 ppm |
| Metal electroplating composition 25 | SYS$^D$2110 | UPD3115 A | UPD3115S | Compound 25 | 1 L | 10 ppm | 100 ppm | 1 ppm |
| Metal electroplating composition 26 | SYS$^D$2110 | UPD3115 A | UPD3115S | Compound 26 | 1 L | 50 ppm | 500 ppm | 5 ppm |
| Metal electroplating composition 27 | SYS$^D$2110 | UPD3115 A | UPD3115S | Compound 27 | 1 L | 100 ppm | 1000 ppm | 10 ppm |
| Metal electroplating composition 28 | SYS$^D$2110 | N,N-dimethyl-disulfenyl carbamic acid-(3-sulfopropyl)ester | Butanol-ethylene oxide-alkylene oxide, Mw = 1000 | Compound 28 | 1 L | 10 ppm | 100 ppm | 1 ppm |

TABLE 1-continued

| Formula No. | Electroplating copper solution | Accelerator | Inhibitor | Leveling agent | Amount of electroplating copper solution | Amount of accelerator | Amount of inhibitor | Amount of leveling agent |
|---|---|---|---|---|---|---|---|---|
| Metal electroplating composition 29 | SYS$^D$2110 | 1-sodium-3-mercapto propane-1-sulfonate | Butanol-ethylene oxide-alkylene oxide, Mw = 3000 | Compound 29 | 1 L | 50 ppm | 500 ppm | 5 ppm |
| Metal electroplating composition 30 | SYS$^D$2110 | 3-(benzothiazolyl-s-sulfenyl)propyl sulfonate sodium salt | Butanol-ethylene oxide-alkylene oxide, Mw = 10000 | Compound 30 | 1 L | 100 ppm | 1000 ppm | 10 ppm |
| Metal electroplating composition 31 | SYS$^D$2110 | UPD3115 A | UPD3115S | Compound 31 | 1 L | 10 ppm | 100 ppm | 1 ppm |
| Metal electroplating composition 32 | SYS$^D$2110 | UPD3115 A | UPD3115S | Compound 32 | 1 L | 50 ppm | 500 ppm | 5 ppm |
| Metal electroplating composition 33 | SYS$^D$2110 | UPD3115 A | UPD3115S | Compound 33 | 1 L | 100 ppm | 1000 ppm | 10 ppm |
| Metal electroplating composition 34 | SYS$^D$2110 | N,N-dimethyl-disulfenyl carbamic acid-(3-sulfopropyl)ester | Butanol-ethylene oxide-alkylene oxide, Mw = 1000 | Compound 34 | 1 L | 10 ppm | 100 ppm | 1 ppm |
| Metal electroplating composition 35 | SYS$^D$2110 | 1-sodium-3-mercapto propane-1-sulfonate | Butanol-ethylene oxide-alkylene oxide, Mw = 3000 | Compound 35 | 1 L | 50 ppm | 500 ppm | 5 ppm |
| Comparative Metal electroplating composition 1 | SYS$^D$2110 | UPD3115 A | UPD3115S | The polymer obtained by the method of Example 1 in CN105705491 A | 1 L | 10 ppm | 100 ppm | 1 ppm |
| Comparative Metal electroplating composition 2 | SYS$^D$2110 | UPD3115 A | UPD3115S | The polymer obtained by the method of Example 2 in CN105705491 A | 1 L | 50 ppm | 500 ppm | 5 ppm |
| Comparative Metal electroplating composition 3 | SYS$^D$2110 | UPD3115 A | UPD3115S | The polymer obtained by the method of Example 3 in CN105705491 A | 1 L | 100 ppm | 1000 ppm | 10 ppm |
| Comparative Metal electroplating composition 4 | SYS$^D$2110 | N,N-dimethyl-disulfenyl carbamic acid-(3-sulfopropyl)ester | Butanol-ethylene oxide-alkylene oxide, Mw = 1000 | The polymer obtained by the method of Example 1 in CN105705491 A | 1 L | 10 ppm | 100 ppm | 1 ppm |

TABLE 1-continued

| Formula No. | Electro-plating copper solution | Accelerator | Inhibitor | Leveling agent | Amount of electroplating copper solution | Amount of accelerator | Amount of inhibitor | Amount of leveling agent |
|---|---|---|---|---|---|---|---|---|
| Comparative Metal electroplating composition 5 | SYS$^D$2110 | 1-sodium-3-mercapto propane-1-sulfonate | Butanol-ethylene oxide-alkylene oxide, Mw = 3000 | The polymer obtained by the method of Example 2 in CN105705491 A | 1 L | 50 ppm | 500 ppm | 5 ppm |
| Comparative Metal electroplating composition 6 | SYS$^D$2110 | 3-(benzothiazolyl-s-sulfenyl)propyl sulfonate sodium salt | Butanol-ethylene oxide-alkylene oxide, Mw = 10000 | The polymer obtained by the method of Example 3 in CN105705491 A | 1 L | 100 ppm | 1000 ppm | 10 ppm |

Application Embodiments 1-35 and Comparative Application Embodiments 1-6

In the present invention, Application embodiments 1-35 and Comparative application embodiments 1-6 are carried out with metal electroplating compositions 1-35 and comparative metal electroplating compositions 1-6, respectively. The parameters of the electroplating process are carried out according to the parameters listed in Table 2.

TABLE 2

| | | Pattern wafer with PVD seed layer (graphics) | | |
|---|---|---|---|---|
| Electroplating target | Electroplating parameters | Step | Current density | Electroplating time | Electroplating temperature |
| Embodiment 1, 4, 7, 10, 13, 16, 19, 22, 25, 28, 31, 34 | Three-step electroplating | Step 1 | 0.1 ASD | 3 s | 20° C. |
| | | Step 2 | 0.5 ASD | 20 s | 20° C. |
| | | Step 3 | 1 ASD | 30 s | 20° C. |
| Embodiment 2, 5, 8, 11, 14, 17, 20, 23, 26, 29, 32, 35 | Three-step electroplating | Step 1 | 0.3 ASD | 10 s | 25° C. |
| | | Step 2 | 1.0 ASD | 25 s | 25° C. |
| | | Step 3 | 5 ASD | 45 s | 25° C. |
| Embodiment 3, 6, 9, 12, 15, 18, 21, 24, 27, 30, 33 | Three-step electroplating | Step 1 | 0.5 ASD | 20 s | 30° C. |
| | | Step 2 | 1.5 ASD | 30 s | 30° C. |
| | | Step 3 | 10 ASD | 60 s | 30° C. |
| Comparative Application Embodiment 1 | Three-step electroplating | Step 1 | 0.1 ASD | 3 s | 20° C. |
| | | Step 2 | 0.5 ASD | 20 s | 20° C. |
| | | Step 3 | 1 ASD | 30 s | 20° C. |
| Comparative Application Embodiment 2 | Three-step electroplating | Step 1 | 0.3 ASD | 10 s | 25° C. |
| | | Step 2 | 1.0 ASD | 25 s | 25° C. |
| | | Step 3 | 5 ASD | 45 s | 25° C. |
| Comparative Application Embodiment 3 | Three-step electroplating | Step 1 | 0.5 ASD | 20 s | 30° C. |
| | | Step 2 | 1.5 ASD | 30 s | 30° C. |
| | | Step 3 | 10 ASD | 60 s | 30° C. |
| Comparative Application Embodiment 4 | Three-step electroplating | Step 1 | 0.1 ASD | 3 s | 20° C. |
| | | Step 2 | 0.5 ASD | 20 s | 20° C. |
| | | Step 3 | 1 ASD | 30 s | 20° C. |

TABLE 2-continued

| | | Pattern wafer with PVD seed layer (graphics) | | | |
|---|---|---|---|---|---|
| Electroplating target | | Electroplating parameters | Current density | Electroplating time | Electroplating temperature |
| Comparative Application Embodiment 5 | Three-step electroplating | Step 1 | 0.3 ASD | 10 s | 25° C. |
| | | Step 2 | 1.0 ASD | 25 s | 25° C. |
| | | Step 3 | 5 ASD | 45 s | 25° C. |
| Comparative Application Embodiment 6 | Three-step electroplating | Step 1 | 0.5 ASD | 20 s | 30° C. |
| | | Step 2 | 1.5 ASD | 30 s | 30° C. |
| | | Step 3 | 10 ASD | 60 s | 30° C. |

Application Effects

The application effect is shown in Table 3. Wherein, the impurity content is analyzed by elemental analysis of combustion method, and the holes condition, the uniform-plating property, the structure compactness and the surface roughness are observed by SEM electron microscopy.

TABLE 3

| No. | Holes condition | Impurity in plated layer (C) | Impurity in plated layer (O) | Impurity in plated layer (S) | uniform-plating property | Structure compactness | Surface roughness |
|---|---|---|---|---|---|---|---|
| Application embodiment 1 | No hole | <20 ppm | <10 ppm | <10 ppm | No orifice bulge | compact | Smooth |
| Application embodiment 2 | No hole | <20 ppm | <10 ppm | <10 ppm | No orifice bulge | compact | Smooth |
| Application embodiment 3 | No hole | <20 ppm | <10 ppm | <10 ppm | No orifice bulge | compact | Smooth |
| Application embodiment 4 | No hole | <20 ppm | <10 ppm | <10 ppm | No orifice bulge | compact | Smooth |
| Application embodiment 5 | No hole | <20 ppm | <10 ppm | <10 ppm | No orifice bulge | compact | Smooth |
| Application embodiment 6 | No hole | <20 ppm | <10 ppm | <10 ppm | No orifice bulge | compact | Smooth |
| Application embodiment 7 | Small holes | <20 ppm | <10 ppm | <10 ppm | Slight orifice bulge | Slightly loose | Slightly rough |
| Application embodiment 8 | No hole | <20 ppm | <10 ppm | <10 ppm | No orifice bulge | compact | Smooth |
| Application embodiment 9 | No hole | <20 ppm | <10 ppm | <10 ppm | No orifice bulge | compact | Smooth |
| Application embodiment 10 | No hole | <20 ppm | <10 ppm | <10 ppm | No orifice bulge | compact | Smooth |
| Application embodiment 11 | Small holes or defects | <20 ppm | <10 ppm | <10 ppm | Slight orifice bulge | Slightly loose | Slightly rough |
| Application embodiment 12 | No hole | <20 ppm | <10 ppm | <10 ppm | No orifice bulge | compact | Smooth |
| Application embodiment 13 | No hole | <20 ppm | <10 ppm | <10 ppm | No orifice orifice bulge | compact | Smooth |
| Application embodiment 14 | No hole | <20 ppm | <10 ppm | <10 ppm | No orifice bulge | compact | Smooth |
| Application embodiment 15 | No hole | <20 ppm | <10 ppm | <10 ppm | No orifice bulge | compact | Smooth |

TABLE 3-continued

| No. | Holes condition | Impurity in plated layer (C) | Impurity in plated layer (O) | Impurity in plated layer (S) | uniform-plating property | Structure compactness | Surface roughness |
|---|---|---|---|---|---|---|---|
| Application embodiment 16 | No hole | <20 ppm | <10 ppm | <10 ppm | No orifice bulge | compact | Smooth |
| Application embodiment 17 | No hole | <20 ppm | <10 ppm | <10 ppm | No orifice bulge | compact | Smooth |
| Application embodiment 18 | No hole | <20 ppm | <10 ppm | <10 ppm | No orifice bulge | compact | Smooth |
| Application embodiment 19 | No hole | <20 ppm | <10 ppm | <10 ppm | No orifice bulge | compact | Smooth |
| Application embodiment 20 | Small holes | <20 ppm | <10 ppm | <10 ppm | Slight orifice bulge | Slightly loose | Slightly rough |
| Application embodiment 21 | No hole | <20 ppm | <10 ppm | <10 ppm | No orifice bulge | compact | Smooth |
| Application embodiment 22 | No hole | <20 ppm | <10 ppm | <10 ppm | No orifice bulge | compact | Smooth |
| Application embodiment 23 | No hole | <20 ppm | <10 ppm | <10 ppm | No orifice bulge | compact | Smooth |
| Application embodiment 24 | No hole | <20 ppm | <10 ppm | <10 ppm | No orifice bulge | compact | Smooth |
| Application embodiment 25 | No hole | <20 ppm | <10 ppm | <10 ppm | No orifice bulge | compact | Smooth |
| Application embodiment 26 | No hole | <20 ppm | <10 ppm | <10 ppm | No orifice bulge | compact | Smooth |
| Application embodiment 27 | No hole | <20 ppm | <10 ppm | <10 ppm | No orifice bulge | compact | Smooth |
| Application embodiment 28 | No hole | <20 ppm | <10 ppm | <10 ppm | No orifice bulge | compact | Smooth |
| Application embodiment 29 | No hole | <20 ppm | <10 ppm | <10 ppm | No orifice bulge | compact | Smooth |
| Application embodiment 30 | Small holes | <20 ppm | <10 ppm | <10 ppm | Slight orifice bulge | Slightly loose | Slightly rough |
| Application embodiment 31 | No hole | <20 ppm | <10 ppm | <10 ppm | No orifice bulge | compact | Smooth |
| Application embodiment 32 | No hole | <20 ppm | <10 ppm | <10 ppm | No orifice bulge | compact | Smooth |
| Application embodiment 33 | No hole | <20 ppm | <10 ppm | <10 ppm | No orifice bulge | compact | Smooth |
| Application embodiment 34 | No hole | <20 ppm | <10 ppm | <10 ppm | No orifice bulge | compact | Smooth |
| Application embodiment 35 | No hole | <20 ppm | <10 ppm | <10 ppm | No orifice bulge | compact | Smooth |
| Comparative application embodiment 1 | Large holes | >20 ppm | >10 ppm | >10 ppm | Obvious orifice bulge | Loose | Rough |
| Comparative application embodiment 2 | Only a few holes | >20 ppm | >10 ppm | >10 ppm | more orifice bulge | Loose | Rough |
| Comparative application embodiment 3 | Only a few holes | >20 ppm | >10 ppm | >10 ppm | more orifice bulge | Loose | Slightly rough |
| Comparative application embodiment 4 | Large holes | >20 ppm | >10 ppm | >10 ppm | Obvious orifice bulge | Loose | Rough |

TABLE 3-continued

| No. | Holes condition | Impurity in plated layer (C) | Impurity in plated layer (O) | Impurity in plated layer (S) | uniform-plating property | Structure compactness | Surface roughness |
|---|---|---|---|---|---|---|---|
| Comparative application embodiment 5 | Only a few holes | >20 ppm | >10 ppm | >10 ppm | more orifice bulge | Loose | Rough |
| Comparative application embodiment 6 | Only a few holes | >20 ppm | >10 ppm | >10 ppm | more orifice bulge | Loose | Slightly rough |

The above embodiments show that using the metal electroplating compositions of the present invention for electroplating can achieve the effects of free of hole or defect, low plating layer impurity, good uniform-plating property, compact structure, and low surface roughness. Meanwhile, the usage of the polymer leveling agent containing imidazole structure disclosed in Patent application No. CN105705491A has the disadvantages of free of holes and defects, high plating layer impurity, poor uniform-plating property, loose structure, high surface roughness.

Although the specific embodiments of the present invention are described above, a person skilled in the art should understand that these are only examples and can be changed or modified in a variety of ways without deviating from the principle and essence of the present invention. Accordingly, the scope of the present invention is defined by the appended claims.

What is claimed is:

1. A metal electroplating composition, wherein a raw material of the metal electroplating composition comprises a leveling agent represented by formula I,

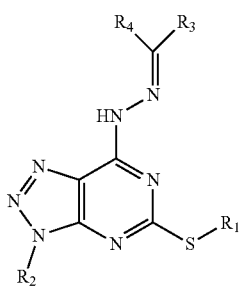

I wherein,
$R_1$ is $C_1$-$C_5$ alkyl, propargyl, allyl or benzyl;
$R_2$ is H, $C_1$-$C_5$ alkyl, hydroxy-substituted $C_1$-$C_5$ alkyl, unsaturated five-membered $C_1$-$C_3$ alkyl substituted by an unsaturated five-membered heterocycle, phenyl, halogenated phenyl, benzyl, halogenated benzyl, or a hydroxyl-substituted benzyl;
$R_3$ is substituted or unsubstituted phenyl, pyridyl, naphthyl, hydroxy-substituted naphthyl, thienyl, furyl or indolyl;
$R_4$ is H or $C_1$-$C_5$ alkyl;
the substituted phenyl includes at least one substituent that is selected from the group consisting of halogen, $C_1$-$C_5$ alkyl, nitro, methoxy, hydroxy and $C_1$-$C_3$ alkylamino, and when the substituted phenyl includes more than one substituent each of the substituents are the same or different;

a heteroatom in the unsaturated five-membered heterocyclic ring is selected from the group consisting of O, N and S, and the number of heteroatoms is 1 to 3, and the heteroatoms are the same or different when there are more than one heteroatoms,
wherein the raw material of the metal electroplating composition comprises a metal electroplating liquid; and the metal electroplating liquid comprises a copper salt, an acidic electrolyte, a halide ion source, and water.

2. The metal electroplating composition according to claim 1, wherein in the leveling agent represented by formula I, at least one of the following is present:
$R_1$ is methyl, propyl, benzyl, propargyl or allyl;
$R_2$ is benzyl, methyl, hydroxyethyl, thiophene-substituted methyl, furan-substituted ethyl, monohalogenated benzyl, or hydroxy-substituted benzyl;
$R_3$ is pyridyl, thienyl, indolyl, naphthyl, hydroxy-substituted naphthyl, phenyl, hydroxy-substituted phenyl, monohalogenated phenyl, methylphenyl, nitrophenyl, methoxyphenyl or dimethylamino phenyl;
$R_4$ is H or methyl; and
the halogen is F, Cl or Br.

3. The metal electroplating composition according to claim 1, wherein the leveling agent represented by formula I selected from the group consisting of
Compound 1: $R_1$=Propyl-; $R_2$=Bn-; $R_3$=Ph-; $R_4$=H—;
Compound 2: $R_1$=Propyl-; $R_2$=Bn-; $R_3$=2-Cl-Ph-; $R_4$=H—;
Compound 3: $R_1$=Propyl-; $R_2$=Bn-; $R_3$=3-Cl-Ph-; $R_4$=H—;
Compound 4: $R_1$=Propyl-; $R_2$=Bn-; $R_3$=4-Cl-Ph-; $R_4$=H—;
Compound 5: $R_1$=Propyl-; $R_2$=Bn-; $R_3$=4-Br-Ph-; $R_4$=H—;
Compound 6: $R_1$=Propyl-; $R_2$=Bn-; $R_3$=2-F-Ph-; $R_4$=H—;
Compound 7: $R_1$=Propyl-; $R_2$=Bn-; $R_3$=4-Me-Ph-; $R_4$=H—;
Compound 8: $R_1$=Propyl-; $R_2$=Bn-; $R_3$=3,4,5-(MeO)$_3$-Ph-; $R_4$=H—;
Compound 9: $R_1$=Propyl-; $R_2$=Bn-; $R_3$=4-NO$_2$-Ph-; $R_4$=H—;
Compound 10: $R_1$=Propyl-; $R_2$=Bn-; $R_3$=4-(N,N—(CH$_3$)$_2$)-Ph-; $R_4$=H—;
Compound 11: $R_1$=Propyl-; $R_2$=Bn-;

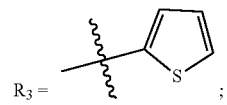 [SMILES: *c1cccs1]

$R_4$=H—;

Compound 12: $R_1$=Propyl-; $R_2$=Bn-;

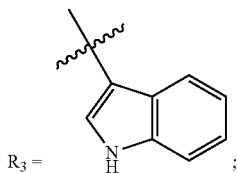 [SMILES: *c1c[nH]c2ccccc12]

$R_4$=H—;

Compound 13: $R_1$=Propyl-; $R_2$=Bn-;

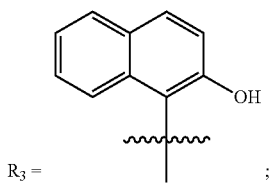

$R_4$=H—;

Compound 14: $R_1$=Propyl-; $R_2$=Bn-;

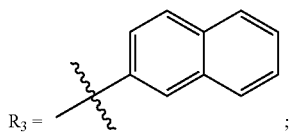

$R_4$=H—;

Compound 15: $R_1$=Propyl-; $R_2$=Bn-;

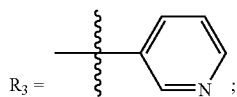

$R_4$=H—;

Compound 16: $R_1$=Propyl-; $R_2$=Bn-; $R_3$=Ph-; $R_4$=$CH_3$—;

Compound 17: $R_1$=Propyl-; $R_2$=Bn-; $R_3$=4-MeO-Ph-; $R_4$=$CH_3$—;

Compound 18: $R_1$=Propyl-; $R_2$=Bn-; $R_3$=2-OH-Ph-; $R_4$=$CH_3$—;

Compound 19: $R_1$=Propyl-; $R_2$=Bn-; $R_3$=4-OH-Ph-; $R_4$=$CH_3$—;

Compound 20: $R_1$=Propyl-; $R_2$=Bn-; $R_3$=4-Br-Ph-; $R_4$=$CH_3$—;

Compound 21: $R_1$=Propyl-;

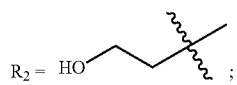

$R_3$=2-OH-Ph-; $R_4$=$CH_3$—;

Compound 22: $R_1$=Propyl-; $R_2$=2-Cl-Bn-; $R_3$=2-OH-Ph-; $R_4$=$CH_3$—;

Compound 23: $R_1$=Propyl-; $R_2$=3-Cl-Bn-; $R_3$=2-OH-Ph-; $R_4$=$CH_3$—;

Compound 24: $R_1$=Propyl-; $R_2$=4-Cl-Bn-; $R_3$=2-OH-Ph-; $R_4$=$CH_3$—;

Compound 25: $R_1$=Propyl-; $R_2$=4-Br-Bn-; $R_3$=2-OH-Ph-; $R_4$=$CH_3$—;

Compound 26: $R_1$=Propyl-; $R_2$=4-F-Bn-; $R_3$=2-OH-Ph-; $R_4$=$CH_3$—;

Compound 27: $R_1$=Propyl-;

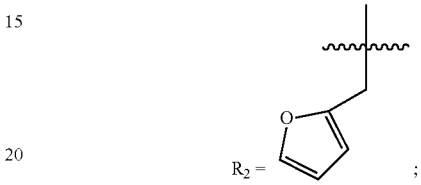

$R_3$=2-OH-Ph-; $R_4$=$CH_3$—;

Compound 28: $R_1$=Propyl-;

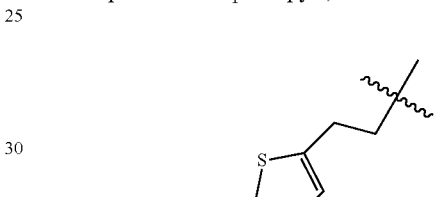

$R_3$=2-OH-Ph-; $R_4$=$CH_3$—;

Compound 29: $R_1$=Propyl-; $R_2$=4-OH-Bn-; $R_3$=2-OH-Ph-; $R_4$=$CH_3$—;

Compound 30: $R_1$=Propargyl-; $R_2$=Bn-; $R_3$=3,4,5-(MeO)$_3$-Ph-; $R_4$=H—;

Compound 31: $R_1$=Propargyl-; $R_2$=Bn-;

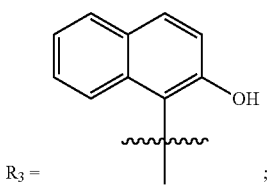 [SMILES: *c1c(O)ccc2ccccc12]

$R_4$=H—;

Compound 32: $R_1$=Propargyl-; $R_2$=Bn-; $R_3$=4-(N,N—($CH_3$)$_2$)-Ph-; $R_4$=H—;

Compound 33: $R_1$=Propargyl-; $R_2$=Bn-; $R_3$=2-OH-Ph-; $R_4$=$CH_3$—;

Compound 34: $R_1$=Bn-; $R_2$=Bn-; $R_3$=3,4,5-(MeO)$_3$-Ph-; $R_4$=H—; and

Compound 35: $R_1$=Bn-; $R_2$=Bn-; $R_3$=2-OH-Ph-; $R_4$=$CH_3$—.

4. The metal electroplating composition according to claim 1, wherein the metal electroplating liquid includes at least one selected from the group consisting of:

the copper salt being selected from the group consisting of copper sulfate, copper halide, copper acetate, copper nitrate, copper fluoroborate, copper alkylsulfonate, copper arylsulfonate, copper sulfamate and copper gluconate;

a molar concentration of copper ions in the metal electroplating liquid being in a range of 0.15-2.85 mol/L;

the acidic electrolyte being selected from the group consisting of sulfuric acid, phosphoric acid, acetic acid, fluoroboric acid, sulfamic acid, alkylsulfonic acid, arylsulfonic acid and hydrochloric acid;

in each liter of the metal electroplating composition, a mass of the acidic electrolyte being 1-300 g;

the halide ion source being a chloride ion source;

a concentration of the halide ion of the halide ion source being 0-100 ppm; and a concentration of the leveling agent being 1-10 ppm.

5. The metal electroplating composition according to claim 4, wherein, the metal electroplating liquid includes at least one selected from the group consisting of:

the copper alkylsulfonate being selected from the group consisting of copper methanesulfonate, copper ethanesulfonate and copper propanesulfonate;

the copper arylsulfonate being selected from the group consisting of copper phenyl sultanate, copper phenolsulfonate and copper p-toluenesulfonate;

the alkylsulfonic acid being selected from the group consisting of methanesulfonic acid, ethanesulfonic acid, propanesulfonic acid and trifluoromethanesulfonic acid;

the arylsulfonic acid being selected from the group consisting of phenylsulfonic acid, phenolsulfonic acid and toluenesulfonic acid;

the chloride ion source being selected from the group consisting of copper chloride, tin chloride and hydrochloric acid;

the concentration of the halide ions of the halide ion source being 50-100 ppm; and the concentration of the leveling agent being 5-10 ppm.

6. The metal electroplating composition according to claim 1, wherein the raw material of the metal electroplating composition comprises at least one of an accelerator and an inhibitor.

7. The metal electroplating composition according to claim 6, wherein when the raw material of the metal electroplating composite comprises the accelerator, a concentration of the accelerator is 0.1 to 1000 ppm and the accelerator is selected from the group consisting of N,N-dimethyl-disulfenylcarbamic acid-(3-sulfopropyl) ester, 3-mercapto-propylsulfonic acid-(3-sulfopropyl) ester, 3-mercapto-propylsulfonate sodium salt; disulfenyl carbonate-o-ethyl ester-s-ester and 3-mercapto-1-propane sultanate potassium salt, disulfopropyl disulfide, 3-(benzothiazolyl-s-sulfenyl)propyl sultanate sodium salt, pyridinium propyl sulfonyl betaine, 1-sodium-3-mercapto propane-1-sulfonate, N,N-dimethyl-disulfenyl carbamic acid-(3-sulfoethyl) ester, 3-mercapto-ethyl propyl sulfonic acid-(3-sulfoethyl) ester, 3-mercapto-ethyl sultanate sodium salt, carbonic acid-disulfenyl-o-ethyl ester-s-ester and 3-mercapto-1-ethanesulfonate potassium salt, disulfoethyl disulfide, 3-(benzothiazolyl-s-sulfenyl)ethyl sultanate sodium salt, pyridinium ethyl sulfonyl betaine and 1-sodium-3-mercaptoethane-1-sulfonate; and wherein when the raw material of the metal electroplating composition comprises the inhibitor, a concentration of the inhibitor is 1 to 10000 ppm and the inhibitor is selected from the group consisting of polypropylene glycol copolymer, polyethylene glycol copolymer, ethylene oxide-propylene oxide copolymer, and butanol-ethylene oxide-propylene oxide copolymer.

8. The metal electroplating composition according to claim 7, wherein when the raw material of the metal electroplating composition comprises the inhibitor, the inhibitor is a butanol-ethylene oxide-propylene oxide copolymer having a weight-average molecular weight of 100-100,000; and the concentration of the inhibitor is 5-10000 ppm.

9. The metal electroplating composition of claim 6, wherein the raw material of the metal electroplating composition consists of the metal electroplating liquid, the leveling agent, the accelerator and the inhibitor.

10. A method for electroplating a substrate, which comprises:

(1) contacting the substrate to be electroplated with the metal electroplating composition according to claim 1;

(2) applying an electric current for electroplating.

11. The method according to claim 10, wherein the method includes at least one selected from the group consisting of:

in step (1), the substrate is a wafer or chip of a printed circuit board or an integrated circuit;

in step (2), the current density of the electroplating is 0.1-10 ASD;

in step (2), the electroplating time is 53-110 s;

in step (2), the electroplating temperature is 10-65° C.

12. The method according to claim 10, wherein step (2) is carried out in three steps:

in a first step, the current density is 0.1-0.5 ASD; the electroplating time is 3-20 s;

and the electroplating temperature is 10-65° C.;

in a second step, the current density is 0.5-1.5 ASD; the electroplating time is 20-30 s; and the electroplating temperature is 10-65° C.;

in a third step, the current density is 1-10 ASD; the electroplating time is 30-60 s;

and the electroplating temperature is 10-65° C.

13. The method according to claim 11, wherein, the method includes at least one selected from the group consisting of:

in step (2), the current density of the electroplating is 0.3-5 ASD;

in step (2), the electroplating time is 80-110 s;

in step (2), the electroplating temperature is 10-35° C.

14. The method according to claim 13, wherein, the method includes at least one selected from the group consisting of:

in step (2), the current density of the electroplating is 0.5-1.5 ASD;

in step (2), the electroplating temperature is 20-30° C.

* * * * *